United States Patent [19]
König et al.

[11] Patent Number: 5,310,769
[45] Date of Patent: May 10, 1994

[54] PROCESS FOR THE PRODUCTION OF POLYAMINE MIXTURES OF THE POLYAMINO-POLYARYL-POLYMETHYLENE SERIES

[75] Inventors: Christian König, Kaarst; Manfred Gallus, Krefeld; Reinhold Wüllner, Krefeld; Franz-Moritz Richter, Marne; Rudolf Uchdorf, Krefeld, all of Fed. Rep. of Germany; William C. Forester, Upter St. Clair, Pa.

[73] Assignees: Bayer Aktiengesellschaft, Leverkusen, Fed. Rep. of Germany; Miles Inc., Pittsburgh, Pa.

[21] Appl. No.: 877,684

[22] Filed: May 1, 1992

[51] Int. Cl.$^5$ .............................................. C08G 18/00
[52] U.S. Cl. ................................... 521/163; 521/155; 564/331; 564/333; 564/335
[58] Field of Search ................ 521/155, 163; 564/331, 564/333, 335

[56] References Cited

U.S. PATENT DOCUMENTS

| | | | |
|---|---|---|---|
| 2,683,730 | 7/1954 | Seeger et al. | 260/453 |
| 4,259,526 | 3/1981 | Dunlap et al. | 564/331 |

FOREIGN PATENT DOCUMENTS

| | | |
|---|---|---|
| 3225135 | 1/1984 | Fed. Rep. of Germany. |
| 1181763 | 2/1970 | United Kingdom. |
| 1378423 | 12/1974 | United Kingdom. |

OTHER PUBLICATIONS

Chemical Abstracts, vol. 86, No. 4, Jan. 24, 1977, Abstract No. 17282s.

*Primary Examiner*—John Kight, III
*Assistant Examiner*—Duc Troung
*Attorney, Agent, or Firm*—Joseph C. Gil; Lyndanne M. Whalen

[57] ABSTRACT

A process for production of polyamines of the diphenylmethane series through a condensation reaction of aniline with formaldehyde in the presence of an acid catalyst, neutralization of the acid catalyst after reaction completion, and distillation of the resultant polyamine mixture is described. The key feature of the process is the abrupt increase in reaction temperature after the condensation reaction or after the first rearrangement step.

10 Claims, No Drawings

PROCESS FOR THE PRODUCTION OF POLYAMINE MIXTURES OF THE POLYAMINO-POLYARYL-POLYMETHYLENE SERIES

BACKGROUND OF THE INVENTION

The present invention relates to an improved process for the production of polyamine mixtures of the polyamino-polyaryl-polymethylene series, as well as to the use thereof in the production of white polyurethane foam materials.

The production of diaminoarylmethane and polyamino-polyaryl-polymethylene mixtures by the acid condensation of aromatic amine and formaldehyde is known (U.S. Pat. No. 2,683,730). The diaminoarylmethane and the polyamine mixtures are valuable as intermediate products in the production of the corresponding isocyanates. Polyurethane foams produced from such isocyanates show a yellow-brown coloration. The coloration of the foam has come to serve as a quality characteristic of the isocyanate used: the darker the coloration, the poorer the isocyanate used.

German Auslegeschrift 3,225,135 describes a process for the production of polyamino polyaryl polymethylenes in which the components are preferably mixed at temperatures of up to 50° C., and in which the reaction mixture is reacted in a tube reactor at a continuously increasing temperature from 50°C. until reaching from 90° C. to 100° C. The polyurethane foam materials produced from the corresponding isocyanates are darkly discolored.

U.S. Pat. No. 4,259,526 describes a special process for the production of polyamino polyaryl polymethylenes, in which the amine is reacted with formaldehyde in the presence of an acid catalyst at 10° C. to 100° C. at a protonation degree of from 0.1 to 25%. Additional acid is added subsequently, and the temperature is adjusted 75° C. to 150° C. The polyamine is then separated. The disadvantage of this process is the expensive separation of the acid catalyst. In addition, the polyurethane foam obtained from the corresponding isocyanate is not light in color.

The object of the present invention was therefore to discover a process which permits production of a high grade isocyanate that results in a light polyurethane foam material.

DESCRIPTION OF THE INVENTION

The above noted goal was achieved by the present invention. More particularly, the present invention is directed to a improved process for the production of polyamine of the diphenylmethane series via condensation of aniline with formaldehyde, continued reaction in the presence of an acid catalyst, neutralization of the acid catalyst after the completed reaction, and purification of the resultant polyamine mixtures by distillation of excess aromatic amines. The present invention requires that:

a) aniline is reacted with formaldehyde in the mole ratio of 1.5:1 to 10:1 at temperatures between 10° and 150° C., b) an acid catalyst is thereafter added to the reaction mixture at a mole ratio of aniline to acid catalyst of from 2:1 to 100:1 (corresponding to a protonation degree of 1 to 50%) and the temperature is from 10° to 150° C., and wherein the water formed during the condensation reaction is removed either before step b) or after step b), c) the temperature of mixture obtained from b) is increased by at least 40° C. in no more than 15 minutes, and thereafter, if necessary, heating of the mixture is continued to a final temperature between 105° and 200° C., with the proviso that the reaction time is from 10 to 300 minutes after the temperature increase, and d) the reaction mixture from c) is distilled after neutralization of the acid catalyst.

The process of the present invention leads to the production of polyamine mixtures of the diphenylmethane series, which following phosgenation produce white polyurethane foam materials.

In a one embodiment of the present invention, formaldehyde can added to the reaction mixture after step a) or b), whereby the aniline to formaldehyde mole ratio that is achieved with both additions is from 1.5:1 to 5.0:1.

In addition, the process can also be carried out as follows:

b) aniline is reacted with an acid catalyst in the mole ratio 2:1 to 100:1 (corresponding to a protonation degree of from 1 to 50%); and a) subsequently, formaldehyde is added to the mixture from b), wherein the mole ratio of aniline to formaldehyde is from 1.5:1 to 10:1 and the temperature is from 10° to 150° C., and thereafter, the reaction steps c) and d) are carried out.

The process of the invention differs from the known processes, in that the temperature of the reaction mixture is abruptly (i.e., in less than 15 minutes) raised by at least 40° C. after the condensation step, or after the first rearrangement, and thereafter the second rearrangement to polyamine is carried out at a final temperature between 105° and 200° C. Surprisingly, it became apparent that the temperature control of the process has considerable influence on the quality of the polyamine mixture produced, and therefore also on the polyurethane foam material produced from the corresponding isocyanate.

The reaction time after the temperature increase of at least 40° C. is also greater than in known processes. In the past, it was believed that a reaction time increase at a higher temperature "at the second rearrangement" would lead to poorer polyamines, that would produce correspondingly darker polyurethane foam materials.

The process of the invention is preferably carried out in such way that the temperature of step a) is between 50° and 120° C. and the mole ratio of aniline to formaldehyde in step a) is between 1.5:1 and 4.0:1.

Hydrochloric acid is preferred as the catalyst.

The mole ratio of aniline to acid catalyst in step b) is preferred to be between 2:1 and 20:1 (corresponding to a protonation degree of from 5 to 50%).

In one preferred embodiment, the temperature prior to step c) is between 35° C. and 60° C. and the final temperature of step c) is between 150° and 180° C.

The polyamine mixture produced by the present process is used to produce the corresponding isocyanate, which in turn is used for the production of light polyurethane foam material.

It is generally known that the acid condensation of aromatic amine and formaldehyde to compounds of the diaminodiphenylmethane series is made in several reaction steps:

A. Condensation

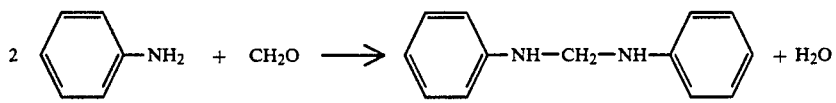

B. First Rearrangement

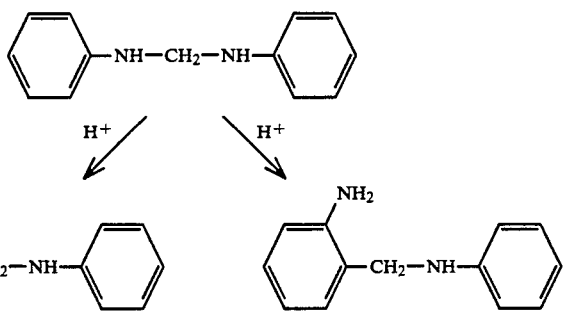

C. Final Rearrangement

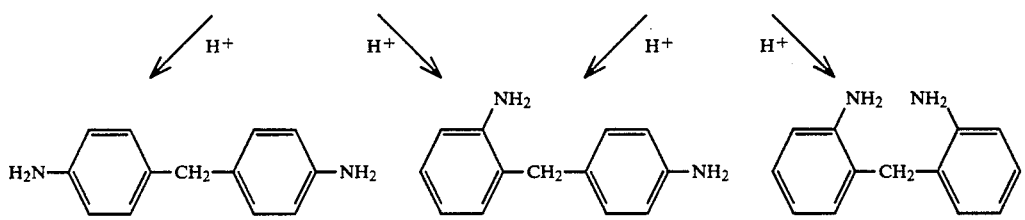

When carrying out the present process, the condensation is generally done by combining aniline and aqueous formaldehyde solution. The aqueous phase is either separated or is left in the mixture. The reaction between the aniline and formaldehyde is exothermic. However, the reaction mixture can be cooled. The reaction is carried out at a temperature of from 10° to 150° C., preferably from 50° to 120° C. As is known in the art, the mole ratio of aniline to formaldehyde will determine the amount of diaminodiphenylmethane compounds in the amine mixture. This mole ratio is generally from 1.5:1 to 10:1 and is preferably from 1.5:1 to 4.0:1.

The condensate is mixed with an acid catalyst, preferably an aqueous HCl-solution in the following step b). This reaction is also exothermic and can be adjusted to the desired temperature by cooling. The temperature is generally between 10° and 150° C., and is preferably between 35° and 60° C. As is generally known in the art, the mole ratio of aniline to acid catalyst will define the amounts of o-substituents and p-substituents in the final product. The mole ratio of aniline to catalyst is generally between 2:1 and 100:1, and preferably between 2:1 and 20:1. These ratios can also be defined as protonation degree. The protonation degree indicates how many parts of aniline in the form of ammonium salts, i.e. in protonated form, are present. The protonation degree is generally between 1% and 50%, is preferably between 5% and 50%. It is insignificant for the process if the reaction water is removed from the system before or after step b).

The combining of the aniline, formaldehyde and acid catalyst can also be made in another step, whereby normally at first aniline salt is formed, and this mixture is reacted with formaldehyde. The various ratios (i.e., aniline to formaldehyde and aniline to acid catalyst), as well as the temperatures are the same as mentioned above.

In addition, more formaldehyde can be added prior, during or after the introduction of the acid catalyst as described in step b). The overall mole ratio of aniline to formaldehyde is from 1.5:1 to 5.0:1 following the total formaldehyde addition.

The temperature increase of at least 40° C. should be made in no more than 15 minutes. A temperature increase to between 105° and 200°, and preferably to between 150° C. and 180°, can then be made. The reaction time after the "abrupt" heating should be from 10 to 300 minutes, depending upon the protonation degree of the acidic reaction solution. The acidic reaction mixture is then neutralized, and the polyamine is stripped from the excess aniline by distillation.

The phosgenation of the polyamine mixtures is carried out based on known technical processes. The polyurethane foams are also produced using well known processes.

The color of polyisocyanato polyaryl polymethylenes can be broken down into two main absorptions in the UV-Visable spectrum - 430 nm and 520 nm, which can be used to predict the coloration of a corresponding foam. Based on experience, the value at 430 nm shows a yellow-brown-coloration while the value at 520 nm shows a grey-coloration of the foam. The lower the absorption value the lighter the coloration of the foam. The invention will be explained in detail with the help of the following examples.

EXAMPLE 1 (COMPARATIVE SAMPLE)

7060 kg/hr aniline and 2970 kg/hr formaldehyde (32% aqueous solution) were mixed and went through a condensation reaction at 80° C. (mole-ratio aniline to formaldehyde equaled 2.3:1). The reaction mixture was discharged into a 8 cubic meter mixing vessel. After separation of the reaction water, 2215 kg/hr HCL (30% aqueous solution) was added (protonation degree equaled 25%), and the temperature was maintained at 40° C. through vacuum cooling. The mixture obtained in this way was then gradually heated up to 55°-75°-105°-120° C. in 5 sequential reaction mixing vessels (8 cubic meters each). The mixture was neutralized with a caustic soda solution, separated from the aqueous salt solution, and distilled to strip the remaining water and excess aniline. The polyamine obtained consisted of 64% by weight diaminodiphenylmethane and 36% by weight of higher oligomers. The isocyanate mixture contained approximately 50% by weight diisocyanatodiphenylmethane after phosgenation of the polyamine. The absorption values of this isocyanate that would correlate with the later coloration of a polyurethane foam produced therefrom were at 0.275 at 430 nm and 0.046 at 520 nm.

EXAMPLE 2 (BASED ON INVENTION)

7060 kg/hr aniline and 2970 kg/hr formaldehyde (32% aqueous solution) were mixed and went through a condensation reaction at 80° C. (mole-ratio aniline to formaldehyde=2.3:1). After the separation of the reaction water, 2215 g/hrs HCl (30% aqueous solution) was added to the reaction mixture in an 8 cubic meter mixing vessel (protonation degree=25%) and the temperature was maintained at 40° C. through vacuum cooling. The mixture obtained was then transferred to an 8 cubic meter stirred reaction vessel whose temperature was maintained at 90° C. and in four following mixing vessels (8 cubic meters each) to the following temperatures 105°-150°-160°-160° C. The mixture was neutralized with a caustic soda solution, separated from the aqueous salt solution, and distilled to strip the remaining water and excess aniline. The polyamine obtained consisted of 64.1% by weight of diaminodiphenylmethane and 35.9% by weight of higher oligomers. After phosgenation, the isocyanate mixture contained approximately 50% by weight diisocyanatodiphenylmethane. The absorption values of this isocyanate, which correlates with the later coloration of a polyurethane foam produced therefrom, were 0.068 at 430 nm and 0.014 at 520 nm.

EXAMPLE 3 (COMPARATIVE EXAMPLE)

5900 kg/hr aniline and 3000 kg/hr formaldehyde (32% aqueous solution) were mixed and went through a condensation reaction at 80° C. (mole ratio aniline to formaldehyde was 1.9:1). 1850 kg/hr HCL (30% aqueous solution) was added into an 8 cubic meter mixing vessel after separation of the reaction water (protonation degree=25%) and the temperature was maintained at 40° C. through vacuum cooling. The mixture obtained in this way was heated up in five reaction vessels arranged in series (8 cubic meters each) to the following temperature levels 55°-70°-140°-150°-150° C. The mixture was neutralized with a caustic soda solution, separated from the aqueous salt solution and distilled to strip the remaining water and excess aniline. The polyamine obtained consisted of 51% by weight diaminodiphenylmethane and 49% by weight of higher oligomers. Following phosgenation, the isocyanate mixtures contained approximately 50% by weight diisocyanatodiphenylmethane. The absorption values of this isocyanate were 0.207 at 430 nm and 0.056 at 520 nm.

EXAMPLE 4 (BASED ON INVENTION)

With otherwise the same test conditions as in Example 3, the temperature in the mixing vessel following the reactor operated at 40° C. was 90° C. The other temperatures in the following four reactors were 105°-140°-150°-150° C. Thereafter, everything was carried out as in Example 3. The absorption values of this isocyanate were 0.105 at 430 nm and 0.028 at 520 nm.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. In a process for production of polyamines of the diphenylmethane series through a condensation reaction of aniline with formaldehyde in the presence of an acid catalyst, neutralization of the acid catalyst after reaction completion, and distillation of the resultant polyamine mixture, the improvement wherein:
   a) aniline is reacted with formaldehyde in the mole ratio of 1.5:1 to 10:1 at temperatures between 10° and 150° C.,
   b) an acid catalyst is thereafter added to the reaction mixture at a mole ratio of aniline to acid catalyst of from 2:1 to 100:1 (corresponding to a protonation degree of 1 to 50%) and the temperature is from 10° to 150° C., and wherein the water formed during the condensation reaction is removed either before step b) or after step b),
   c) the temperature of the mixture obtained from b) is increased by at least 40° C. in no more 15 minutes, and thereafter, if necessary, heating of the mixture is continued to a final temperature between 105° and 200° C., with the proviso that the reaction time is from 10 to 300 minutes after the temperature increase, and
   d) the reaction mixture from c) is distilled after neutralization of the acid catalyst.

2. The process of claim 1, wherein after step a) or or during step b), additional formaldehyde is added to the reaction mixture, whereby the mole ratio of aniline to formaldehyde is between 1.5:1 and 5.0:1.

3. The process of claim 1, wherein first,
   a) aniline is reacted with an acid catalyst in the mole ratio 2:1 to 100:1 (corresponding to a protonation degree of 1 to 50%), and then b) formaldehyde is added to the mixture from b), whereby the mole ratio of aniline to formaldehyde is 1.5:1 to 10:1 and the temperature is between 10° and 150° C.

4. The process of claim 1, wherein the temperature of step a) is between 50° and 120° C.

5. The process of claim 1, wherein the mole ratio of aniline to formaldehyde in step a) is from 1.5:1 to 4.0:1.

6. The process of claim 1, wherein in step b) hydrochloric acid is used as the catalyst.

7. The process of claim 1, wherein the mole ratio aniline to acid catalyst in step b) is 2:1 to 20:1 (corresponding to a protonation degree of 5 to 50%).

8. The process of claim 1, wherein the temperature prior to step c) is between 35° and 60° C.

9. The process of claim 1, wherein the final temperature of step c) is between 150° and 180° C.

10. In the preparation of a polyurethane foam form a polyisocyanate, the improvement wherein the isocyanate is the phosgenation product of the process of claim 1.

* * * * *